United States Patent
Tanaka et al.

(10) Patent No.: US 10,851,034 B2
(45) Date of Patent: Dec. 1, 2020

(54) METHOD OF REMOVING 2-CHLORO-1,3,3,3-TETRAFLUOROPROPENE AND METHOD OF PRODUCING 1-CHLORO-2,3,3,3-TETRAFLUOROPROPENE

(71) Applicant: AGC INC., Chiyoda-ku (JP)

(72) Inventors: Toshiyuki Tanaka, Chiyoda-ku (JP); Yasuhiro Suzuki, Chiyoda-ku (JP); Jumpei Nomura, Chiyoda-ku (JP)

(73) Assignee: AGC INC., Chiyoda-ku (JP)

( * ) Notice: Subject to any disclaimer, the term of this patent is extended or adjusted under 35 U.S.C. 154(b) by 0 days.

(21) Appl. No.: 16/904,734

(22) Filed: Jun. 18, 2020

(65) Prior Publication Data

US 2020/0317592 A1    Oct. 8, 2020

Related U.S. Application Data

(63) Continuation of application No. PCT/JP2018/045932, filed on Dec. 13, 2018.

(30) Foreign Application Priority Data

Dec. 21, 2017 (JP) ................. 2017-245340

(51) Int. Cl.
   *C07C 17/395* (2006.01)
   *C07C 21/18* (2006.01)
(52) U.S. Cl.
   CPC ............ *C07C 17/395* (2013.01); *C07C 21/18* (2013.01)

(58) Field of Classification Search
   CPC ............................ C07C 21/18; C07C 17/395
   See application file for complete search history.

(56) References Cited

U.S. PATENT DOCUMENTS 10,370,313 B2 *  8/2019  Taniguchi ............. C07C 17/386

FOREIGN PATENT DOCUMENTS

WO    WO 2012/157763 A1    11/2012

OTHER PUBLICATIONS

International Search Report dated Mar. 5, 2019 in PCT/JP2018/045932 filed Dec. 13, 2018, 1 page.

* cited by examiner

*Primary Examiner* — Jafar F Parsa
(74) *Attorney, Agent, or Firm* — Oblon, McClelland, Maier & Neustadt, L.L.P.

(57) ABSTRACT

Provided are: a method of removing 2-chloro-1,3,3,3-tetrafluoropropene (1224xe), the method including bringing a mixture containing 1224xe and 1224yd into contact with an alkali optionally in the presence of a phase transfer catalyst; and a method of producing 1-chloro-2,3,3,3-tetrafluoropropene (1224yd), the method including bringing a mixture containing 1224xe and 1224yd into contact with an alkali optionally in the presence of a phase transfer catalyst.

14 Claims, 1 Drawing Sheet

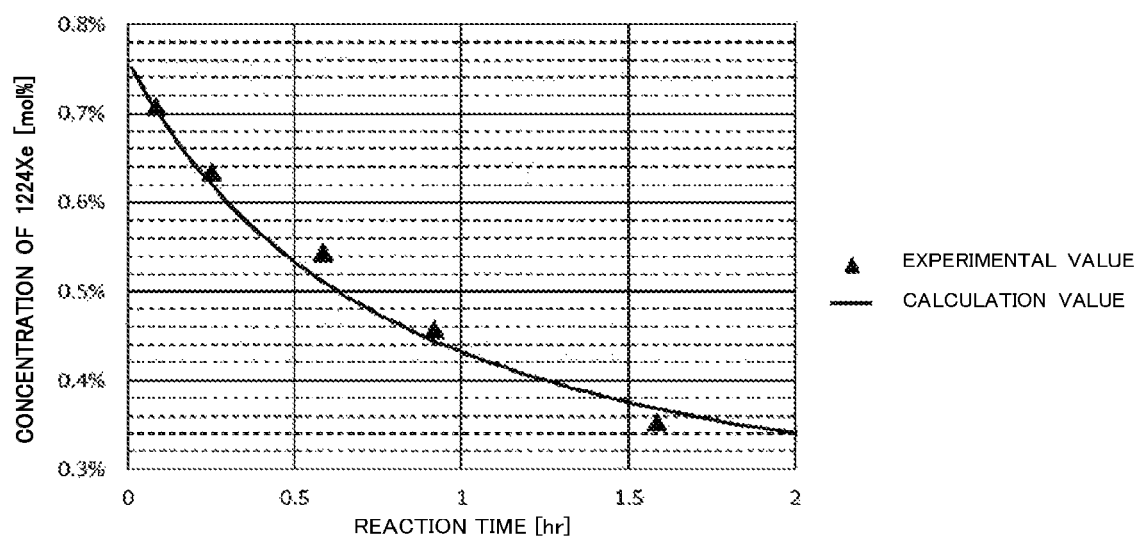

METHOD OF REMOVING 2-CHLORO-1,3,3,3-TETRAFLUOROPROPENE AND METHOD OF PRODUCING 1-CHLORO-2,3,3,3-TETRAFLUOROPROPENE

CROSS-REFERENCE TO RELATED APPLICATIONS

This application is a Continuation Application of International Application No. PCT/JP2018/045932, filed Dec. 13, 2018, the disclosure of which is incorporated herein by reference in its entirety. Further, this application claims priority from Japanese Patent Application No. 2017-245340, filed Dec. 21, 2017, the disclosure of which is incorporated herein by reference in its entirety.

TECHNICAL FIELD

The present invention relates to a method of removing 2-chloro-1,3,3,3-tetrafluoropropene and a method of producing 1-chloro-2,3,3,3-tetrafluoropropene.

BACKGROUND ART

Chlorofluorocarbons (CFC) such as chlorotrifluoromethane (CFC-13) or dichlorodifluoromethane (CFC-12) or hydrochlorofluorocarbons (HCFC) such as chlorodifluoromethane (HCFC-22) has been conventionally used as working media for a heat cycle such as a coolant for a refrigerator, a coolant for an air conditioner, working media for a power generation system (waste heat recovery power generation, etc.), working media for a latent heat transport device (heat pipe, etc.), or a secondary cooling medium. However, effect of CFC and HCFC on the ozone layer in the stratosphere has been pointed out, and these are currently subject to regulations.

Under such circumstances, hydrofluorocarbons (HFC) such as difluoromethane (HFC-32), tetrafluoroethane (HFC-134), or pentafluoroethane (HFC-125), which has little effect on the ozone layer, namely has a low ozone depleting potential (ODP), are used as working media for heat cycle in place of CFC or HCFC. For example, in a centrifugal refrigerator used for air-conditioning of a building or for an industrial chilling water production plant, the employed working medium has been changed from trichlorofluoromethane (CFC-11) to 1,1,1,2-tetrafluoroethane (HFC-134a), 1,1,1,3,3-pentafluoropropane (HFC-245fa), or the like. Also, for example, R410A (a near-azeotropic refrigerant mixture of HFC-32 and HFC-125 at a mass ratio of 1/1) is a coolant which has been heretofore widely used. However, it has been pointed out that HFC may also cause global warming. Therefore, there is a pressing need to develop a working medium for heat cycle, which has little effect on the ozone layer and a global warming potential (GWP) of which is low.

In recent years, hydrofluoroolefins (HFO), hydrochlorofluoroolefins (HCFO), chlorofluoroolefins (CFO) and the like, each of which having a carbon-carbon double bond that is easily decomposed by an OH radical in the atmosphere, attract much attention as promising working media having little effect on the ozone layer and low GWP. Herein, "HFC" means a saturated HFC unless otherwise specified, and discriminated from HFO. In some cases, HFC may be specified as a saturated hydrofluorocarbon.

Among these, HCFO and CFO, which are compounds having suppressed inflammability due to the high content of halogens in a molecule thereof, are therefore currently studied for application as working media which exhibit reduced load on the environment and suppressed inflammability. For example, Patent Document 1 describes a working medium using 1-chloro-2,3,3,3-tetrafluoropropene ($CF_3$—CF=CHCl; HCFO-1224yd).

CITATION LIST

Patent Document

[Patent Document 1] International Publication No. WO 2012/157763

SUMMARY OF INVENTION

Technical Problem

In this regard, 1-chloro-2,3,3,3-tetrafluoropropene ($CF_3$—CF=CHCl; HCFO-1224yd; hereinafter also referred to as "1224yd") may be produced by various methods. However, impurities are always present in the product even if any of the producing methods are employed. Among such impurities, it has come to be known that 2-chloro-1,3,3,3-tetrafluoropropene ($CF_3$—CCl=CHF; HCFO-1224xe; hereinafter referred to as "1224xe") destabilizes 1224yd. Therefore, it is required to minimize a content of 1224xe in the resultant obtained by the 1224yd production.

However, the present inventors have confirmed that 1224xe cannot be sufficiently removed from a mixture containing 1224yd and 1224xe, even when a general purification treatment such as distillation or extraction is applied, because 1224yd and 1224xe are similar to each other in terms of boiling point and chemical structure.

In view of the above, the invention aims to provide a method of removing 1224xe by which a concentration of 1224xe in a mixture of 1224xe and 1224yd obtained in a production of 1224yd or the like can be remarkably reduced. In addition, the invention aims to provide a method of producing 1224yd which can improve, by means of reduction of impurities accompanying 1224yd, especially 1224xe, stability of 1224yd when 1224yd is used for an application such as a working medium.

Means to Solve the Problem

The invention provides a method of removing 1224xe having a configuration of any one of the following [1] to [7] and a method of producing 1224yd having a configuration of any one of the following [8] to [14].

[1] A method of removing 1224xe, the method comprising bringing a mixture comprising 1224xe and 1224yd into contact with an alkali.

[2] The method of removing according to [1], further comprising:

bringing an isomer mixture of dichloropentafluoropropane comprising 1,1-dichloro-2,2,3,3,3-pentafluoropropane ($CHCl_2CF_2CF_3$; HCFC-225ca; herein also referred to as "225ca") and 1,2-dichloro-1,2,3,3,3-pentafluoropropane ($CHClFCClFCF_3$; HCFC-225ba; herein also referred to as "225ba") into contact with an aqueous alkali solution in the presence of a phase transfer catalyst to yield a composition comprising 1,1-dichloro-2,3,3,3-tetrafluoropropene ($CF_3$—CF=$CCl_2$; CFO-1214ya; herein also referred to as "1214ya") and 1,2-dichloro-1,3,3,3-tetrafluoropropene ($CF_3$—CCl=CClF; CFO-1214xb; herein also referred to as "1214xb"); and subsequently, bringing the composition into contact with hydrogen in the presence of a catalyst to yield the mixture.

[3] The method of removing according to [1] or [2], wherein the contact between the mixture and the alkali is performed at a temperature of from 40° C. to 90° C.

[4] The method of removing according to any one of [1] to 3, wherein the alkali comprises at least one selected from an alkali metal hydroxide or an alkaline earth metal hydroxide.

[5] The method of removing according to any one of [1] to [4,] wherein the contact between the mixture and the alkali is performed in the presence of a phase transfer catalyst.

[6] The method of removing according to any one of [1] to [5], wherein a proportion of 1224xe with respect to a total amount of 1224xe and 1224yd in the mixture is 50 mol % or less.

[7] The method of removing according to any one of [1] to [6], wherein a proportion of 1224xe with respect to a total amount of 1224xe and 1224yd in a mixture prepared by bringing the mixture into contact with the alkali is 0.5 mol % or less.

[8] A method of producing 1224yd, the method comprising:
bringing a mixture comprising 1224xe and 1224yd into contact with an alkali, thereby removing 1224xe from the mixture.

[9] The method of producing according to [8], further comprising:
bringing an isomer mixture of dichloropentafluoropropane comprising 225ca and 225ba into contact with an aqueous alkali solution in the presence of a phase transfer catalyst to yield a composition comprising 1,1-dichloro-2,3,3,3-tetrafluoropropene and 1,2-dichloro-1,3,3,3-tetrafluoropropene; and
subsequently, bringing the composition into contact with hydrogen in the presence of a catalyst to yield the mixture.

[10] The method of producing according to [8] or [9], wherein the contact between the mixture and the alkali is performed at a temperature of from 40° C. to 90° C.

[11] The method of producing according to any one of [8] to [10], wherein the alkali comprises at least one selected from an alkali metal hydroxide or an alkaline earth metal hydroxide.

[12] The method of producing according to any one of [8] to [11], wherein the contact between the mixture and the alkali is performed in the presence of a phase transfer catalyst.

[13] The method of producing according to any one of [8] to [12], wherein a proportion of 1224xe with respect to a total amount of 1224xe and 1224yd in the mixture is 50 mol % or less.

[14] The method of producing according to any one of [8] to [13], wherein a proportion of 1224xe with respect to a total amount of 1224xe and 1224yd in a mixture prepared by bringing the mixture into contact with the alkali is 0.5 mol % or less.

Herein, with respect to a halogenated hydrocarbon, an abbreviation of the compound is denoted in parentheses after the compound name, and if necessary, the abbreviation may be used instead of the compound name. Further, as an abbreviation, only the portion of the number and the lowercase letters of the alphabet which follows the hyphen (-) may be used. Further, with respect to a compound which has a double bond in the molecule, and therefore has an E-isomer and a Z-isomer such as 1224yd and 1224xe, the E-isomer and the Z-isomer are identified by denoting (E) or (Z) at the end of the abbreviation. When there is no specific notation with respect to E-isomer or Z-isomer in the name, or its abbreviation of the compound, the name or the abbreviation means a collective term including the E-isomer and the Z-isomer, as well as a mixture of the E-isomer and the Z-isomer.

Herein, a numerical range expressed by "(from) x to y" includes the values of x and y in the range as the minimum and maximum values, respectively.

Effects of Invention

According to the removing method of the invention, the concentration of 1224xe in the mixture of 1224xe and 1224yd obtained in the production of 1224yd or the like can be remarkably reduced. In addition, according to the method of producing 1224yd of the invention, stability of 1224yd which is to be used for an application such as a working medium can be improved by reducing impurities accompanying 1224yd, especially 1224xe. In other words, according to the method of producing 1224yd of the invention, 1224yd with a low concentration of impurity 1224xe and an improved stability can be produced.

BRIEF DESCRIPTION OF DRAWINGS

FIG. 1 is a graph showing the relationship between the reaction time and the concentration of 1224xe in a dehydrochlorination reaction of 1224xe.

DESCRIPTION OF EMBODIMENTS

Method of Removing 1224xe (First Embodiment)

A first embodiment of the invention relates to a method of reducing a concentration of 1224xe in a mixture (hereinafter, referred to as "first mixture") containing 2-chloro-1,3,3,3-tetrafluoropropene ($CF_3$—CCl=CHF, 1224xe), and 1-chloro-2,3,3,3-tetrafluoropropene ($CF_3$—CF=CHCl, 1224yd). The term "remove" herein encompass not only taking away a certain compound in its own state from a mixture but also eliminating the compound by converting it into another compound by a reaction or the like.

Specifically, it is a method which includes bringing the first mixture into contact with an alkali to cause a reaction of dehydrochlorination of 1224xe in the first mixture to convert 1224xe into 1,3,3,3-tetrafluoropropyne as shown in Formula (1) below, thereby removing 1224xe from the first mixture, so as to yield another mixture (hereinafter referred to as "second mixture"), which has a reduced proportion of 1224xe with respect to the total amount of 1224xe and 1224yd as compared to that of the first mixture.

From the above, the concentration of 1224xe can be reduced without substantially reducing the concentration of 1224yd in the first mixture containing 1224yd and 1224xe. In this regard, 1,3,3,3-tetrafluoropropyne obtained by a dehydrochlorination reaction of 1224xe is not a compound that makes 1224yd unstable. Therefore, the second mixture may, but preferably should not, contain 1,3,3,3-tetrafluoropropyne. Such 1224yd and 1,3,3,3-tetrafluoropropyne can be easily separated by a common method such as distillation.

(First Mixture)

A first mixture used in the first embodiment of the invention contains 1224yd and 1224xe.

The 1224yd in the first mixture may be a mixture of Z-isomer and E-isomer, solely Z-isomer, or solely E-isomer. 1224yd has a high proportion of halogens which suppress inflammability, and further has a carbon-carbon double bond in a molecule which is easily decomposed by an OH radical in the atmosphere. Therefore, the inflammability of 1224yd is low, the effect of 1224yd on the ozone layer is little, and the GWP of 1224yd is small. Therefore, 1224yd is highly useful as a cleaning agent, a working medium such as a coolant, a blowing agent, a solvent, and an aerosol.

According to the invention, 1224yd is obtained, for example, by: using an isomer mixture of dichloropentafluoropropane (HCFC-225) containing 225ca and 225ba (hereinafter referred to as "isomer mixture of HCFC-225") as a source material; bringing it into contact with an aqueous alkali solution in the presence of a phase transfer catalyst to prepare a composition containing 1214ya and 1214xb; and bringing the composition containing 1214ya and 1214xb into contact with hydrogen in the presence of a catalyst, as described below.

In the aforementioned method of producing 1224yd using the isomer mixture of HCFC-225 as a source material, impurities such as 1224xe may be by-produced besides 1224yd, and a mixture containing 1224xe and 1224yd may be obtained. According to the invention, for example, such a mixture containing 1224xe and 1224yd may be used as the first mixture. In the first mixture, 1224xe may be a mixture of Z-isomer and E-isomer, solely Z-isomer, or solely E-isomer.

In the first mixture used in the invention, a proportion of 1224xe with respect to a total amount of 1224xe and 1224yd is preferably 50 mol % or less, more preferably 30 mol % or less, further preferably 20 mol % or less, and particularly preferably 10 mol % or less. In other words, the proportion of 1224yd with respect to the total amount of 1224xe and 1224yd in the first mixture is preferably 50 mol % or more, more preferably 70 mol % or more, further preferably 80 mol % or more, and particularly preferably 90 mol % or more.

There is no particular restriction on the lower limit of the proportion of 1224xe with respect to the total amount of 1224xe and 1224yd in the first mixture, and it is, for example, about 0.5 mol %.

(Contacting Step with Alkali)

The method of the invention includes a step of bringing the first mixture into contact with an alkali (hereinafter, also referred to as "alkali contacting step"). A dehydrochlorination reaction of 1224xe can occur by the contact of the first mixture with an alkali in the alkali contacting step. In this regard, it has been known that 1224yd causes a dehydrofluorination reaction when contacting with an alkali. However, the inventors have found that the dehydrochlorination reaction of 1224xe advances in preference to the dehydrofluorination reaction of 1224yd, when the first mixture, in which both 1224yd and 1224xe are present, is brought into contact with an alkali.

Therefore, at the alkali contacting step in the method of the invention, 1224xe can be reduced without reducing the 1224yd because a dehydrofluorination reaction of 1224yd does not substantially occur. As a result, 1224xe is removed from the first mixture, and a second mixture, in which the proportion of 1224xe with respect to the total amount of 1224xe and 1224yd is reduced compared to the first mixture, namely the proportion of 1224yd with respect to the total amount of 1224xe and 1224yd is increased, can be obtained.

The dehydrochlorination reaction of 1224xe at the alkali contacting step may be represented by the following chemical equation (1).

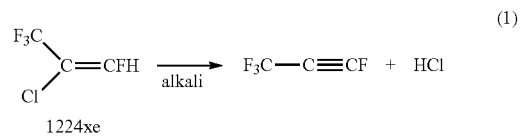

According to the invention, the alkali contacting step may be performed in either a gas phase or a liquid phase. The alkali contacting step is preferably performed in a liquid phase, because it enables efficient dehydrochlorination reaction of 1224xe and use of a smaller sized reactor can be employed compared to that used in a gas phase reaction, which is more advantageous in terms of industrial operation. In this regard, performing the alkali contacting step in a gas phase means that 1224xe in a gas state is reacted using the first mixture which is gaseous, and performing the alkali contacting step in a liquid phase means that 1224xe in a liquid state is reacted using the first mixture which is a liquid.

When the alkali contacting step according to the invention is carried out in a gas phase, examples thereof include a method in which the first mixture in a gas state is brought into contact with a solid state, preferably a powdery state alkali.

When the alkali contacting step according to the invention is carried out in a liquid phase, examples thereof include a method in which the first mixture in a liquid state is brought into contact with an alkali dissolved in a solvent, that is an alkali in a solution state. For example, it is preferable that a solution obtained by dissolving the alkali in a solvent and the first mixture are brought into contact with each other by means of stirring or the like.

There is no particular restriction on the alkali, insofar as it can carry out the dehydrochlorination reaction of 1224xe through contact with the first mixture. The alkali is preferably at least one selected from the group consisting of a metal hydroxide, a metal oxide, and a metal carbonate. Examples of the alkali include an alkali metal and an alkaline earth metal, as well as a hydroxide, oxide, or carbonate thereof.

When the alkali is a metal hydroxide, examples thereof include an alkaline earth metal hydroxide and an alkali metal hydroxide. Examples of the alkaline earth metal hydroxide include magnesium hydroxide, calcium hydroxide, strontium hydroxide, and barium hydroxide. Examples of the alkali metal hydroxide include lithium hydroxide, sodium hydroxide, and potassium hydroxide.

As the alkali used in the producing method of the invention, a metal hydroxide of an alkali metal or an alkaline earth metal is preferable from the viewpoints of reaction time and reaction yield, and at least one selected from the group consisting of potassium hydroxide and sodium hydroxide is particularly preferable. The metal hydroxide which is the alkali metal or the alkaline earth metal may be used singly or in combination of two or more kinds thereof.

When the alkali contacting step in the invention is performed in a liquid phase, there is no particular restriction on a solvent used for preparing an alkali in a solution state, insofar as it can dissolve a predetermined amount of the alkali, and does not react with the first mixture. For example, water is preferable as the solvent from the viewpoint that it can sufficiently dissolve an alkali metal hydroxide and it causes no side reaction derived from the solvent.

The alkali contacting step is preferably carried out under a condition in which the dehydrochlorination reaction of 1224xe in the first mixture proceeds in preference to the dehydrofluorination reaction of 1224yd. Such a condition may be appropriately set in consideration of the respective reaction rate constants for the dehydrochlorination reaction of 1224xe and the dehydrofluorination reaction of 1224yd in the presence of an alkali. By performing the alkali contacting step under the condition, a second mixture in which the proportion of 1224xe with respect to the total amount of 1224xe and 1224yd is reduced compared to the first mixture, in other words, a second mixture in which the proportion of 1224yd with respect to the total amount of 1224xe and 1224yd is increased, is obtained.

From the above viewpoint, an alkali in the alkali contacting step is preferably in such an amount that the proportion of the mass of the alkali such as an alkali metal hydroxide with respect to the total amount (mass) of a solvent and the alkali is from 1% by mass to 30% by mass, and more preferably from 5% by mass to 15% by mass. When a phase transfer catalyst is used, the amount of an alkali may be calculated by deeming the phase transfer catalyst as a solvent. In other words, when a phase transfer catalyst is used, it is preferable that the proportion of an alkali with respect to the total amount of a solvent (including the phase transfer catalyst) and an alkali is within the above range. When the amount of an alkali is below the above range, there may be a case in which a sufficient reaction rate is not obtained in the dehydrochlorination reaction of 1224xe. On the other hand, when the amount of an alkali exceeds the above range, the dehydrofluorination reaction of 1224yd may take place.

From the above viewpoint, the amount of an alkali in the contacting step is preferably from 1 to 60 parts by mass per 100 parts by mass as the total amount of 1224xe and 1224yd in the first mixture.

From the above viewpoint, a temperature of the alkali contacting step in the invention in a case in which the step is carried out in a liquid phase is preferably from 40° C. to 90° C., and more preferably from 60° C. to 75° C. When the temperature at the alkali contacting step is lower than 40° C., there may be a case in which a sufficient reaction rate is not obtained in the dehydrochlorination reaction of 1224xe. On the other hand, when the temperature at the alkali contacting step exceeds 90° C., the dehydrofluorination reaction of 1224yd may take place.

A contact time of the alkali contacting step in the invention in a case in which the step is carried out in a liquid phase is preferably from 0.5 to 20 hours, and more preferably from 1 to 10 hours from the aforementioned viewpoint and the viewpoint of securing the productivity, although it may be further subject to the temperature and the concentration of an aqueous alkali solution.

When the alkali contacting step in the invention is carried out in a liquid phase, an additional substance which does not impair the effect of the invention may exist in the reaction system in order to promote the reaction. For example, when an alkali solution using a highly hydrophilic solvent is used as the alkali solution, it is preferable that a phase transfer catalyst or a water-soluble organic solvent which can dissolve 1224yd and 1224xe is present as such an additional substance. It is particularly preferable that a phase transfer catalyst is present in the alkali contacting step.

Examples of the phase transfer catalyst include a quaternary ammonium salt, a quaternary phosphonium salt, a quaternary arsonium salt, a sulfonium salt, and a crown ether, and a quaternary ammonium salt is preferable.

When the phase transfer catalyst is a quaternary ammonium salt, examples thereof include a compound represented by the following Formula (i) (hereinafter, also referred to as "compound (i)").

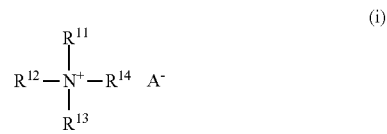

In Formula (i), $R^{11}$ to $R^{14}$ each independently represent a monovalent hydrocarbon group or a monovalent hydrocarbon group to which a functional group that is inert in the reaction is bonded; and $A^-$ represents an anion. $A^-$s in Formula (i) and Formulas (ii) to (iv) described below may be the same or different.

When $R^{11}$ to $R^{14}$ are a hydrocarbon group, examples thereof include an alkyl group, a cycloalkyl group, an alkenyl group, a cycloalkenyl group, and an aryl group, among which an alkyl group and an aryl group are preferable. A number of carbon atoms in $R^{11}$ to $R^{14}$ is preferably from 1 to 20, and more preferably from 1 to 10. $R^{11}$ to $R^{14}$ may be the same or different groups.

When $R^{11}$ to $R^{14}$ are a monovalent hydrocarbon group to which a functional group inert in the reaction is bonded, the functional group may be appropriately selected depending on the reaction conditions. Examples thereof include a halogen atom, an alkoxycarbonyl group, an acyloxy group, a nitrile group, an acyl group, a carboxyl group, and an alkoxyl group.

Examples of $R^{11}R^{12}R^{13}R^{14}N^+$ include tetramethylammonium, tetraethylammonium, tetra-n-propylammonium, tetra-n-butylammonium, methyltri-n-octylammonium, cetyltrimethylammonium, benzyltrimethylammonium, benzyltriethylammonium, cetylbenzyldimethylammonium, cetylpyridinium, n-dodecylpyridinium, phenyltrimethyl ammonium, phenyltriethyl ammonium, N-benzylpicolinium, pentamethonium, and hexamethonium.

Examples of $A^-$ include a chlorine ion, a fluorine ion, a bromine ion, an iodine ion, a sulfate ion, a nitrate ion, a phosphate ion, a perchlorate ion, a hydrogen sulfate ion, a hydroxide ion, an acetate ion, a benzoate ion, a benzenesulfonate ion, and a p-toluenesulfonate ion; and a chlorine ion, a bromine ions, an iodine ions, a hydrogen sulfate ion, and a hydroxide ion are preferable.

As the compound (i), a combination of the following $R^{11}R^{12}R^{13}R^{14}N^+$ and the following $A^-$ is preferable from the viewpoints of versatility and reactivity.

$R^{11}R^{12}R^{13}R^{14}N^+$: tetramethylammonium, tetraethylammonium, tetra-n-propylammonium, tetra-n-butylammonium, or methyltri-n-octylammonium.

$A^-$: fluorine ion, chlorine ion, bromine ion, iodine ion, or hydroxide ion.

As the quaternary ammonium salt, tetra-n-butylammonium chloride (TBAC), tetra-n-butyl ammonium bromide (TBAB), and methyltri-n-octylammonium chloride (TOMAC) are preferable.

When the phase transfer catalyst is a quaternary phosphonium salt, examples thereof include a compound represented by the following Formula (ii).

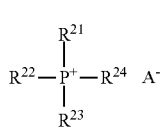

(ii)

In Formula (ii), $R^{21}$ to $R^{24}$ each independently represent a monovalent hydrocarbon group; and $A^-$ represents an anion.

Examples of a hydrocarbon group represented by $R^{21}$ to $R^{24}$ include an alkyl group, a cycloalkyl group, an alkenyl group, a cycloalkenyl group, and an aryl group, among which an alkyl group and an aryl group are preferable. A number of carbon atoms in $R^{21}$ to $R^{24}$ is preferably from 1 to 20, and more preferably from 1 to 10.

Examples of the quaternary phosphonium ($R^{21}R^{22}R^{23}R^{24}P^+$) in Formula (ii) include tetraethylphosphonium, tetra-n-butylphosphonium, ethyltri-n-octylphosphonium, cetyltriethylphosphonium, cetyltri-n-butylphosphonium, n-butyltriphenylphosphonium, n-amyltriphenylphosphonium, methyltriphenylphosphonium, benzyltriphenylphosphonium, and tetraphenylphosphonium.

Examples of $A^-$ include a chlorine ion, a fluorine ion, a bromine ion, an iodine ion, a sulfate ion, a nitrate ion, a phosphate ion, a perchlorate ion, a hydrogen sulfate ion, a hydroxide ion, an acetate ion, a benzoate ion, a benzene sulfonate ion, and a p-toluenesulfonate ion; and a fluorine ion, a chlorine ion, and a bromine ion are preferable.

When the phase transfer catalyst is a quaternary arsonium salt, examples thereof include a compound represented by the following Formula (iii).

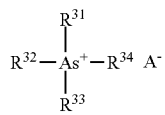

(iii)

In Formula (iii), $R^{31}$ to $R^{34}$ each independently represent a monovalent hydrocarbon group; and $A^-$ represents an anion.

Examples of the hydrocarbon group represented by $R^{31}$ to $R^{34}$ include an alkyl group, a cycloalkyl group, an alkenyl group, a cycloalkenyl group, and an aryl group, among which an alkyl group and an aryl group are preferable. A number of carbon atoms in $R^{31}$ to $R^{34}$ is preferably from 1 to 20, and more preferably from 1 to 10.

As $A^-$, a halogen ion is preferable, and a fluorine ion, a chlorine ion, and a bromine ion are more preferable.

Examples of the quaternary arsonium salt represented by Formula (iii) include triphenylmethylarsonium fluoride, tetraphenylarsonium fluoride, triphenylmethylarsonium chloride, tetraphenylarsonium chloride, and tetraphenylarsonium bromide. As the quaternary arsonium salt, triphenylmethylarsonium chloride is particularly preferable.

When the phase transfer catalyst is a sulfonium salt, examples thereof include a compound represented by the following Formula (iv).

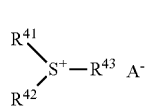

(iv)

In Formula (iv), $R^{41}$ to $R^{43}$ each independently represent a monovalent hydrocarbon group, and $A^-$ represents an anion.

Examples of the hydrocarbon group represented by $R^{41}$ to $R^{43}$ include an alkyl group, a cycloalkyl group, an alkenyl group, a cycloalkenyl group, and an aryl group, among which an alkyl group and an aryl group are preferable. A number of carbon atoms in $R^{41}$ to $R^{43}$ is preferably from 1 to 20, and more preferably from 1 to 10.

As $A^-$ a halogen ion is preferable, and a fluorine ion, a chlorine ion, and a bromine ion are more preferable.

Examples of the sulfonium salt represented by Formula (iv) include di-n-butylmethylsulfonium iodide, tri-n-butylsulfonium tetrafluoroborate, dihexylmethylsulfonium iodide, dicyclohexylmethylsulfonium iodide, dodecylmethylethylsulfonium chloride, and tris(diethylamino)sulfonium difluorotrimethylsilicate. As the sulfonium salt, dodecylmethylethylsulfonium chloride is particularly preferable.

Examples of the crown ether include 18-crown-6, dibenzo-18-crown-6, and dicyclohexyl-18-crown-6.

An amount of the phase transfer catalyst is preferably from 0.001 to 5 parts by mass, and more preferably from 0.01 to 2 parts by mass per 100 parts by mass as the total amount of 1224xe and 1224yd in the first mixture. When the amount of a phase transfer catalyst is too small, there may be a case in which a sufficient reaction rate is not obtained, meanwhile when a larger amount thereof is used, a reaction promoting effect corresponding to the amount used cannot be obtained, which is disadvantageous in terms of cost.

When the reaction system is separated into an aqueous phase and an organic phase, a water-soluble organic solvent (for example, tetraglyme) may be added to the reaction system in place of a phase transfer catalyst so as to make the organic phase and the aqueous phase containing a base compatible, or the phase transfer catalyst and the water-soluble organic solvent may be used in combination.

The water-soluble organic solvent is preferably a solvent which is an organic solvent capable of dissolving 1224yd and 1224xe, and does not affect the reaction according to the invention. Specifically, tetraethylene glycol dimethyl ether (tetraglyme), sulfolane, t-butanol, and the like are preferable. The water-soluble solvent is generally compatible with a basic solution.

An amount of the water-soluble organic solvent is preferably from 1 to 200 parts by mass, and more preferably from 10 to 100 parts by mass per 100 parts by mass as the total amount of 1224xe and 1224yd in the first mixture. When the amount of the water-soluble organic solvent is less than the above range, there may be a case in which a sufficient reaction rate is not obtained. When the amount of the water-soluble organic solvent exceeds the above range, the concentration of an alkali is reduced, and therefore the reaction rate is reduced and the effect of accelerating the reaction corresponding to the amount used cannot be obtained.

When the phase transfer catalyst or the water-soluble organic solvent is used, after introduction into a reactor, it is preferable to bring it into sufficient contact with compounds involved in a reaction by a general stirring means.

A reaction rate constant k of the dehydrochlorination reaction of 1224xe in a case where the alkali contacting step of the first mixture is performed in an aqueous solution of sodium hydroxide in the presence of the aforementioned phase transfer catalyst may be defined by the following Equation (E1).

$$d[1224xe]/dt=k[1224xe][NaOH] \qquad (E1)$$

(In Equation (E1), [1224xe] is a molar concentration of 1224xe in the first mixture containing 1224xe and 1224yd, and [NaOH] is a molar concentration of sodium hydroxide in the aqueous phase. The "d[1224xe]/dt" is a temporal change of the molar concentration of 1224xe in the liquid phase.)

A reaction rate constant k may be obtained according to the Equation (E1) based on results obtained by measuring a reaction time and [1224xe] at different temperatures after bringing the first mixture containing 1224xe and 1224yd into contact with an aqueous solution of sodium hydroxide with a predetermined concentration in the presence of a phase transfer catalyst. The reaction rate constant k in a case where tetra-n-butylammonium bromide (TBAB) was used as the phase transfer catalyst under the conditions that TBAB was contained in the liquid phase at 0.013 mol/L was obtained as a function of temperature T (K), namely k=1.3× $10^{18}$×exp(−1.7×$10^4$/T), by the method using Equation (E1) and the Arrhenius equation.

Similarly, a reaction rate constant of a dehydrofluorination reaction of 1224yd in a case where the first mixture containing 1224xe and 1224yd is brought into contact with an alkali in the presence of a phase transfer catalyst may be obtained in the same manner as described above. Further, the reaction rate constants for cases in which the kind and concentration of a phase transfer catalyst and the kind of an alkali are varied may be similarly obtained by performing a dehydrofluorination reaction of 1224yd using such phase transfer catalyst and alkali and calculating the decomposition rate of 1224yd. Based on the obtained reaction rate constants, the conditions of the alkali contacting step can be set in accordance with the reactor size or the required removal rate of 1224xe, within the aforementioned preferable ranges of the temperature and the concentration of the aqueous alkali solution.

The alkali contacting step in the invention may be performed in a batchwise process, in a semi-continuous process, or in a continuous flow process. The contact time can be appropriately adjusted according to each process. There is no particular restriction on the materials of the reactor used for the alkali contacting step, insofar as it is inert in the reaction solution components including 1224yd, 1224xe, a phase transfer catalyst, a water-soluble organic solvent, an alkali, and a solvent for forming a solution thereof, and a reaction product, and is a corrosion-resistant material. Examples thereof include glass, iron, nickel, and an alloy such as stainless steel containing iron or the like as the main component.

When the alkali contacting step in the invention is performed in a liquid phase, the reaction solution is left to stand after the completion of the alkali contacting step so as to be separated into an organic phase and an aqueous phase. The organic phase may contain unreacted 1224xe, 1,3,3,3-tetrafluoropropyne which is formed by dehydrochlorination of 1224xe, or the like besides the target substance 1224yd. When recovering 1224yd from the organic phase containing these, it is preferable to adopt a general separation and purification method such as distillation.

According to the invention, the proportion of 1224xe with respect to the total amount of 1224xe and 1224yd in the second mixture after the alkali contacting step is preferably 0.5 mol % or less, and more preferably 0.05 mol % or less. In other words, the proportion of 1224yd with respect to the total amount of 1224xe and 1224yd in the second mixture is preferably 99.5 mol % or higher, and more preferably 99.95 mol % or higher.

Method of Producing 1224yd (Second Embodiment)

The method of producing 1224yd of the invention (second embodiment) includes a step of bringing a first mixture containing 1224xe and 1224yd into contact with an alkali. According to the method of producing 1224yd of the invention, 1224xe can be selectively removed from the first mixture by the step of bringing the first mixture into contact with an alkali. The step of bringing the first mixture into contact with an alkali in the second embodiment may be carried out in the same manner as at the alkali contacting step in the method of removing 1224xe (the first embodiment), including a preferable mode.

The method of producing 1224yd of the invention preferably has a step of preparing a first mixture containing 1224xe and 1224yd described below and a step of bringing the first mixture into contact with an alkali. In the preferable mode of the method of producing 1224yd of the invention, the first mixture containing 1224xe and 1224yd is prepared, and then the first mixture is subject to the alkali contacting step, so that a second mixture in which the proportion of 1224xe with respect to the total amount of 1224xe and 1224yd is reduced compared to that of the first mixture and the stability of 1224yd therein is increased can be obtained with a high productivity.

(Step of Obtaining First Mixture)

The step of preparing the first mixture includes bringing an isomer mixture of dichloropentafluoropropane including 225ca and 225ba (isomer mixture of HCFC-225) with an aqueous alkali solution in the presence of a phase transfer catalyst to yield a composition containing 1214ya and 1214xb by dehydrofluorination (hereinafter also referred to as "dehydrofluorination step"), and subsequently bringing the composition containing 1214ya and 1214xb into contact with hydrogen in the presence of a catalyst to yield a first mixture containing 1224xe and 1224yd (hereinafter also referred to as "hydrogen reduction step").

(1) Dehydrofluorination Step

An isomer mixture of HCFC-225 to be used in the dehydrofluorination step includes 225ca and 225ba. The isomer mixture of HCFC-225 may include an isomer of dichloropentafluoropropane other than 225ca and 225ba such as 1,3-dichloro-1,2,2,3,3-pentafluoropropane (CHClFCF$_2$CClF$_2$, HCFC-225cb), 2,2-dichloro-1,1,3,3,3-pentafluoropropane (CHF$_2$CCl$_2$CF$_3$, HCFC-225aa), and 2,3-dichloro-1,1,2,3,3-pentanfluoropropane (CHF$_2$CClFCClF$_2$, HCFC-225bb). An isomer mixture of HCFC-225 to be used in the invention, for example, consists of 225 ca and 225ba, or consists of 225 ca, 225ba, and one or more kinds of isomers of dichloropentafluoropropane other than 225 ca and 225ba, but not limited thereto.

The isomer mixture of HCFC-225 is prepared, for example, by reacting tetrafluoroethylene with dichlorofluoromethane in the presence of a catalyst such as aluminum chloride.

As the isomer mixture of HCFC-225, any isomer mixture of HCFC-225 prepared by a method other than the above method may be used, insofar as it is an isomer mixture containing 225ca and 225ba.

Further, it is possible to use an isomer mixture of HCFC-225 which has been subject to an isomerization reaction in the presence of a Lewis acid catalyst such as aluminum chloride or a metal oxide catalyst to increase its 225ca content as compered to that in the source material. As the metal oxide catalyst, an oxide of at least one element selected from the group consisting of Al, Sb, Nb, Ta, W, Re, B, Sn, Ga, In, Zr, Hf, and Ti may be used.

225ca in the isomer mixture of HCFC-225 is converted to 1214ya by the dehydrofluorination step, and the 1214ya is converted to the target substance 1224yd by the hydrogen reduction step. Meanwhile, 225ba is converted to 1214xb by the dehydrofluorination step, and the 1214xb is converted to 1224xe by the hydrogen reduction step. In this connection, the isomer mixture of HCFC-225 is used for producing 1224yd, because it is usually difficult to completely isolate individual compounds, in this case 225ca which is a source material of 1224yd, from HCFC-225 obtained as an isomer mixture.

A content of 225ca in an isomer mixture of HCFC-225 is, for example, from the viewpoint of efficiently yielding the target substance 1224yd, preferably from 10 to 99 mol % with respect to a total amount of the isomer mixture.

Further, a content of 225ba in the isomer mixture of HCFC-225 is, for example, from the viewpoint of reducing an amount of 1224xe by-produced in the step of producing 1224yd, preferably from 0.1 to 20 mol % with respect to a total amount of the isomer mixture.

As shown in the following chemical equation (2-1), at the dehydrofluorination step in the second embodiment of the invention, the isomer mixture of HCFC-225 is brought into contact with an aqueous alkali solution in the presence of a phase transfer catalyst to cause a dehydrofluorination reaction of 225ca contained in the isomer mixture of HCFC-225 to yield 1214ya. Tetrabutylammonium bromide (TBAB) is preferable as the phase transfer catalyst.

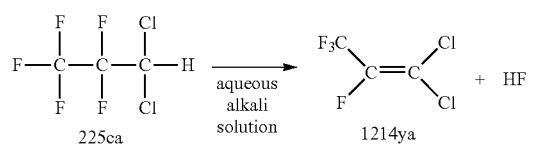

(2-1)

As shown in the chemical equation (2-1), 225ca in the isomer mixture of HCFC-225 undergoes dehydrofluorination by a phase transfer catalyst to yield 1214ya. After the reaction, the obtained 1214ya can be separated and recovered by a known method such as distillation.

However, a composition obtained through the dehydrofluorination of the HCFC-225 isomer mixture (composition containing 1214ya) contains, in addition to 1214ya, 1214xb, which is formed by dehydrofluorination of 225ba in the HCFC-225 isomer mixture. The dehydrofluorination reaction of 225ba is shown in the following chemical equation (2-2).

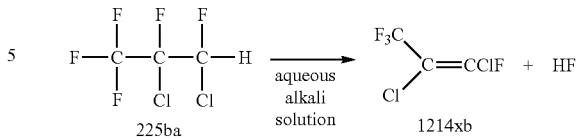

(2-2)

The boiling point of 1214ya is about 44° C., and the boiling point of 1214xb is about 47° C. Therefore, it is difficult to completely separate 1214ya and 1214xb by ordinary distillation. Even if the concentration of 1214ya in a composition containing 1214ya and 1214xb is increased by distillation, 1214xb remains unavoidably. A content of 1214xb in the composition containing 1214ya and 1214xb after distillation is, for example, about 10 mol % or less with respect to a total molar amount of the compounds contained in the composition. This 1214xb is converted to 1224xe in the hydrogen reduction step described below.

(2) Hydrogen Reduction Step

Next, a hydrogen reduction step, in which the composition containing 1214ya and 1214xb obtained as set forth above is brought into contact with hydrogen in the presence of a catalyst (for example, palladium catalyst), is carried out. In the hydrogen reduction step, 1224yd is formed from 1214ya in the composition containing 1214ya and 1214xb, and 1224xe is formed from 1214xb in the same composition respectively to give a first mixture containing 1224yd and 1224xe.

The reaction between 1214ya and hydrogen in the hydrogen reduction step is shown in the following chemical equation (3-1). Further, the reaction between 1214xb and hydrogen is shown in the following chemical equation (3-2).

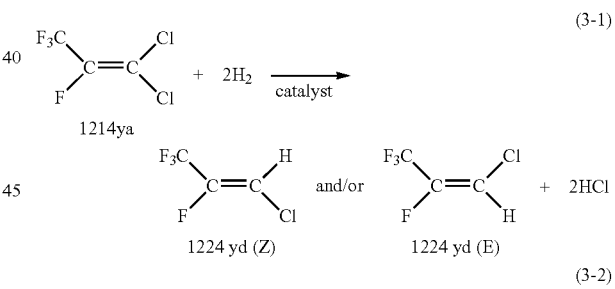

(3-1)

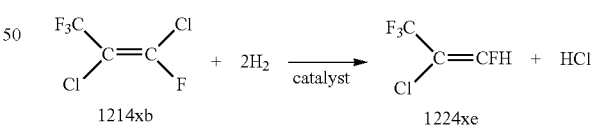

(3-2)

Examples of a specific method of the hydrogen reduction step include a method in which a reactor made of, for example, glass, iron, nickel, or an alloy containing any of these as the main component is packed with a catalyst to form a catalyst layer, and the composition containing 1214ya and 1214xb obtained in the dehydrofluorination step (1) (hereinafter, also referred to as composition (X)) and hydrogen which are in a gaseous form are introduced into the catalyst layer. At this time, in order to control the maximum temperature of the catalyst layer, an inert gas such as nitrogen, a rare gas (helium, argon, etc.), carbon dioxide, or a chlorofluorocarbon, which is inert in the hydrogenation reaction, may be introduced into the catalyst layer in addition to the composition (X) and hydrogen.

A reaction temperature at which the composition (X) is brought into contact with hydrogen to cause a reduction reaction is set above a dew point of a mixed gas of the composition (X) and hydrogen to be used in the reaction when the reaction is performed in a gas phase. When an inert gas is further used, the temperature is set above a dew point of a mixed gas of the composition (X), hydrogen, and the inert gas. In the producing method of the invention, for example, the reaction temperature at the hydrogen reduction step is preferably 200° C. or less.

A produced gas after the reaction at the hydrogen reduction step may include, in addition to 1224yd and 1224xe, unreacted 1214ya and 1214xb, 2,3,3,3-tetrafluoropropene ($CF_3CF=CH_2$, HFO-1234yf) which is an over-reductant, 1,1,1,2-tetrafluoropropane ($CF_3CHFCH_3$, HFC-254eb), 1,1,1-trifluoropropane ($CF_3CH_2CH_3$, HFC-263fb), 3,3,3-trifluoropropene ($CF_3CH=CH_2$, HFO-1243zf), and the like, as well as hydrogen chloride (HCl).

According to the invention, the produced gas may be used as it is as the first mixture in the following alkali contacting step (3), or components other than 1224yd and 1224xe may be appropriately removed from the produced gas to prepare the first mixture to used in the following alkali contacting step (3).

(3) Alkali Contacting Step

In the second embodiment of the invention, a proportion of 1224xe with respect to a total amount of 1224xe and 1224yd in a first mixture to be used at the alkali contacting step is preferably 50 mol % or less, more preferably 30 mol % or less, further preferably 20 mol % or less, and particularly preferably 10 mol % or less. In other words, a proportion of 1224yd with respect to a total amount of 1224xe and 1224yd in the first mixture is preferably 50 mol % or more, more preferably 70 mol % or more, further preferably 80 mol % or more, and particularly preferably 90 mol % or more. Although there is no particular restriction on a lower limit of the proportion of 1224xe with respect to the total amount of 1224xe and 1224yd in the first mixture, it is, for example, about 0.5 mol %.

In the second embodiment of the invention, the alkali contacting step for bringing the first mixture into contact with an alkali may be performed in the same manner as the alkali contacting step in the first embodiment. At the alkali contacting step, 1224xe is removed from the first mixture, and a second mixture in which the proportion of 1224xe with respect to a total amount of 1224xe and 1224yd is reduced compared to that in the first mixture, in other words a proportion of 1224yd with respect to a total amount of 1224xe and 1224yd is increased, can be obtained.

In the second embodiment of the invention, the proportion of 1224xe with respect to the total amount of 1224xe and 1224yd in the second mixture after the alkali contacting step is preferably 0.5 mol % or less, and more preferably 0.05 mol % or less. In other words, the proportion of 1224yd with respect to the total amount of 1224xe and 1224yd in the second mixture is preferably 99.5 mol % or higher, and more preferably 99.95 mol % or higher.

(4) 1224yd Purifying Step

In the second embodiment of the invention, the second mixture after the alkali contacting step may contain, besides the target substance 1224yd, unreacted 1224xe, 1,3,3,3-tetrafluoropropyne generated by dehydrochlorination of 1224xe, etc. Therefore, it is preferable to increase the concentration of 1224yd in the second mixture by subjecting the second mixture after the alkali contacting step to a usual purification treatment such as distillation.

A concentration of 1224yd in the purified 1224yd obtained by purifying the second mixture after the alkali contacting step as described above is preferably 99% by mass or more. 0.1% by mass or less, and preferably 0.01% by mass or less, is attainable as the concentration of 1224xe in the purified 1224yd.

When an acid such as HCl, water, or oxygen is contained in the purified 1224yd, there may be a risk that use of such a purified 1224yd may cause corrosion of an equipment or use of such a purified 1224yd may reduce stability of a working medium composed of the purified 1224yd. Therefore, an acid content thereof, that is, a content of chlorine ions and fluorine ions thereof is preferably less than 10 ppm by mass, more preferably less than 1 ppm by mass, and most preferably less than 0.1 ppm by mass with respect to a total amount of the purified 1224yd. Further, a water content in the purified 1224yd is preferably less than 1000 ppm by mass, and most preferably less than 100 ppm by mass. An oxygen concentration in the purified 1224yd is preferably 1000 ppm by mass or less, and more preferably 500 ppm by mass or less. Outside the above ranges, there may be a case in which degradation of 1224yd occurs or performance of degreasing and cleaning is impaired.

According to the second embodiment of the invention, a purified 1224yd in which a content of an impurity 1224xe is reduced may be obtained, therefore the stability of the purified 1224yd can be improved. Consequently, when it is applied to a cleaning agent, a coolant, a blowing agent, a solvent, or an aerosol, benefit of the product may be increased.

EXAMPLES

The invention will be described in detail below with reference to Examples, provided that the invention is not restricted thereby.

Example 1

A reaction test was performed using a 1 L-volume autoclave equipped with a stirrer and a dip pipe for sampling. First, an aqueous solution of sodium hydroxide (NaOH), an aqueous solution of catalyst in which TBAB (phase transfer catalyst) was dissolved in water, and ion-exchanged water in predetermined amounts were charged in the autoclave in a state of reduced pressure. Next, an organic layer containing 1224xe and 1224yd (first mixture) was supplied into the autoclave. The NaOH was prepared such that a concentration in the aqueous layer reached 9% by mass. Further, the TBAB was added such that TBAB reached 0.013 mol/L with respect to a total amount of a liquid phase in the autoclave (0.8 parts by mass per 100 parts by mass as the total amount of 1224xe and 1224yd).

The first mixture containing 1224xe and 1224yd was prepared by bringing an isomer mixture of HCFC-225 into contact with an aqueous alkali solution in the presence of a phase transfer catalyst to cause a dehydrofluorination reaction to yield a composition containing 1214ya and 1214xb, and then bringing the composition containing 1214ya and 1214xb into contact with hydrogen in the presence of a catalyst. The respective proportions of 1224xe and 1224yd with respect to the total amount of 1224xe and 1224yd in the first mixture were 0.75 mol % and 99.25 mol %.

The autoclave charged with the organic layer containing 1224xe and 1224yd as described above was immersed in a water bath at a predetermined temperature, and when the temperature in the autoclave reached a target temperature (reaction temperature: 65° C.), stirring was started to initiate the reaction.

After the initiation of the reaction, sampling was performed from the dip pipe after elapse of each predetermined time, and after separation into two layers of an organic layer and an aqueous layer, component contents (mol %) of the organic layer were analyzed by gas chromatography based on % by area. From the proportion of the remaining 1224xe, the proportion of the initially charged 1224xe and the reaction rate, the degradation rate of 1224xe was determined. In this regard, a column DB-1301 (trade name, manufactured by Agilent Technologies, Inc., length: 60 m×inner diameter 250 μm×thickness 1 μm) was used for the gas chromatography. Similarly, the degradation rate of 1224yd was also determined. The relationships of the reaction time with the concentration (mol %) of the remaining 1224xe and the concentration (mol %) of the 1224yd are shown in Table 1 and FIG. 1. The proportion of 1224xe (mol %) with respect to the total amount of 1224yd and 1224xe contained in the organic layer is also shown in Table 1.

Using the reaction rate coefficient $k=1.3\times10^{18}\times \exp(-1.7\times 10^4/T)$ obtained using the Equation (E1), the concentration of the remaining 1224xe with respect to the time from the initiation of the reaction was calculated. The results are shown in FIG. 1. In FIG. 1, the solid line shows the concentration value of the remaining 1224xe calculated from the reaction rate constant obtained as described above (calculation value), and the plotted triangles show the concentration value of the remaining 1224xe actually measured as described above (experimental value).

The recovery rate by mass of the mixture containing 1224xe and 1224yd at 1.5 hours after the reaction initiation was 99%, and no degradation of 1224yd was observed.

TABLE 1

| Reaction time | Concentration [mol %] | | |
|---|---|---|---|
| [hr] | 1224xe | 1224yd | 1224xc/(1224xe + 1224yd) × 100 |
| 0 | 0.71 | 93.62 | 0.75 |
| 0.17 | 0.63 | 93.64 | 0.67 |
| 0.50 | 0.54 | 93.62 | 0.58 |
| 0.83 | 0.46 | 93.66 | 0.49 |
| 1.50 | 0.35 | 93.69 | 0.38 |

As shown in Table 1 and FIG. 1, according to the method of removing 1224xe of the invention, the concentration of 1224xe in a first mixture containing 1224yd and 1224xe can be extremely reduced by conducting a dehydrochlorination reaction on 1224xe in the first mixture.

Example 2

When only the reaction temperature was changed from 65° C. to 100° C. using the same reaction device as in Example 1, the concentration of 1224yd was kept at 94% and did not change at the reaction time of 2 hours, however the recovery rate by mass of the mixture containing 1224xe and 1224yd dropped to 85%. Sodium fluoride was generated in the aqueous layer, suggesting that degradation of 1224yd by a dehydrofluorination reaction took place.

The relationships of the reaction time with the concentration of the remaining 1224xe and the concentration of the 1224yd in Example 2 are shown in Table 2. The proportion of 1224xe (mol %) with respect to the total amount of 1224yd and 1224xe contained in the organic layer is also shown in Table 2. Although this suggests that degradation of 1224yd occurs when reacted at 100° C., it is understood that that the concentration of 1224xe in the first mixture can be extremely reduced.

TABLE 2

| Reaction time | Concentration [mol %] | | |
|---|---|---|---|
| [hr] | 1224xe | 1224yd | 1224xe/(1224xe + 1224yd) × 100 |
| 0 | 0.71 | 93.62 | 0.75 |
| 2.00 | 0.01 | 94.02 | 0.01 |

What is claimed is:

1. A method of removing 2-chloro-1,3,3,3-tetrafluoropropene, the method comprising bringing a first mixture comprising 2-chloro-1,3,3,3-tetrafluoropropene and 1-chloro-2,3,3,3-tetrafluoropropene into contact with an alkali.

2. The method according to claim 1, further comprising:
bringing an isomer mixture of di chl oropentafluoropropane comprising 1,1-dichloro-2,2,3,3,3-pentafluoropropane and 1,2-dichloro-1,2,3,3,3-pentafluoropropane into contact with an aqueous alkali solution in the presence of a first phase transfer catalyst to yield a composition comprising 1,1-dichloro-2,3,3,3-tetrafluoropropene and 1,2-dichloro-1,3,3,3-tetrafluoropropene; and subsequently, bringing the composition into contact with hydrogen in the presence of a catalyst to yield the first mixture.

3. The method according to claim 1, wherein the contact between the first mixture and the alkali is performed at a temperature of from 40° C. to 90° C.

4. The method according to claim 1, wherein the alkali comprises at least one selected from an alkali metal hydroxide or an alkaline earth metal hydroxide.

5. The method according to claim 1, wherein the contact between the first mixture and the alkali is performed in the presence of a second phase transfer catalyst.

6. The method according to claim 1, wherein a proportion of 2-chloro-1,3,3,3-tetrafluoropropene with respect to a total amount of 2-chloro-1,3,3,3-tetrafluoropropene and 1-chloro-2,3,3,3-tetrafluoropropene in the first mixture is 50 mol % or less.

7. The method according to claim 1, wherein a proportion of 2-chloro-1,3,3,3-tetrafluoropropene with respect to a total amount of 2-chloro-1,3,3,3-tetrafluoropropene and 1-chloro-2,3,3,3-tetrafluoropropene in a second mixture prepared by bringing the first mixture into contact with the alkali is 0.5 mol % or less.

8. A method of producing 1-chloro-2,3,3,3-tetrafluoropropene, the method comprising:
bringing a first mixture comprising 2-chloro-1,3,3,3-tetrafluoropropene and 1-chloro-2,3,3,3-tetrafluoropropene into contact with an alkali, thereby removing 2-chloro-1,3,3,3-tetrafluoropropene from the first mixture.

9. The method according to claim 8, further comprising:
bringing an isomer mixture of dichloropentafluoropropane comprising 1,1-dichloro-2,2,3,3,3-pentafluoropropane and 1,2-dichloro-1,2,3,3,3-pentafluoropropane into contact with an aqueous alkali solution in the presence of a first phase transfer catalyst to yield a composition comprising 1,1-dichloro-2,3,3,3-tetrafluoropropene and 1,2-dichloro-1,3,3,3-tetrafluoropropene; and subsequently, bringing the composition into contact with hydrogen in the presence of a catalyst to yield the first mixture.

10. The method according to claim 8, wherein the contact between the first mixture and the alkali is performed at a temperature of from 40° C. to 90° C.

11. The method according to claim 8, wherein the alkali comprises at least one selected from an alkali metal hydroxide or an alkaline earth metal hydroxide.

12. The method according to claim 8, wherein the contact between the first mixture and the alkali is performed in the presence of a second phase transfer catalyst.

13. The method according to claim 8, wherein a proportion of 2-chloro-1,3,3,3-tetrafluoropropene with respect to a total amount of 2-chloro-1,3,3,3-tetrafluoropropene and 1-chloro-2,3,3,3-tetrafluoropropene in the first mixture is 50 mol % or less.

14. The method according to claim 8, wherein a proportion of 2-chloro-1,3,3,3-tetrafluoropropene with respect to a total amount of 2-chloro-1,3,3,3-tetrafluoropropene and 1-chloro-2,3,3,3-tetrafluoropropene in a second mixture prepared by bringing the first mixture into contact with the alkali is 0.5 mol % or less.

\* \* \* \* \*